(12) United States Patent
Eskling et al.

(10) Patent No.: US 8,022,039 B2
(45) Date of Patent: Sep. 20, 2011

(54) IMMUNOGENIC HER-2 VARIANTS

(75) Inventors: Marie Eskling, Horsholm (DK); Klaus Gregorius Nielsen, Soborg (DK)

(73) Assignee: BN ImmunoTherapeutics, Inc., Mountain View, CA (US)

( * ) Notice: Subject to any disclaimer, the term of this patent is extended or adjusted under 35 U.S.C. 154(b) by 0 days.

(21) Appl. No.: 12/824,420

(22) Filed: Jun. 28, 2010

(65) Prior Publication Data
US 2010/0285071 A1 Nov. 11, 2010

Related U.S. Application Data

(62) Division of application No. 10/560,961, filed as application No. PCT/DK2004/000451 on Jun. 24, 2004, now Pat. No. 7,763,452.

(60) Provisional application No. 60/482,315, filed on Jun. 25, 2003.

(30) Foreign Application Priority Data

Jun. 25, 2003 (DK) .................................. 2003 00954

(51) Int. Cl.
| | | |
|---|---|---|
| *A61K 38/16* | (2006.01) | |
| *A61K 38/17* | (2006.01) | |
| *C07K 14/00* | (2006.01) | |
| *C07K 14/435* | (2006.01) | |
| *C07K 14/705* | (2006.01) | |

(52) U.S. Cl. ...................................... 514/21.2; 530/350
(58) Field of Classification Search ........................ None
See application file for complete search history.

(56) References Cited

U.S. PATENT DOCUMENTS

| 5,976,546 | A | 11/1999 | Laus et al. | |
|---|---|---|---|---|
| 7,005,498 | B1 * | 2/2006 | Steinaa et al. | 530/324 |
| 7,763,452 | B2 * | 7/2010 | Eskling et al. | 435/252.3 |
| 2006/0008465 | A1 | 1/2006 | Steinaa et al. | |
| 2006/0240511 | A1 | 10/2006 | Eskling et al. | |

FOREIGN PATENT DOCUMENTS

| WO | WO 95/05849 A1 | 3/1995 |
|---|---|---|
| WO | WO 97/24438 A1 | 7/1997 |
| WO | WO 00/20027 * | 4/2000 |
| WO | WO 00/20027 A1 | 4/2000 |
| WO | WO 00/44899 A1 | 8/2000 |
| WO | WO 03/087338 A2 | 10/2003 |
| WO | WO 20041113377 A1 | 12/2004 |

OTHER PUBLICATIONS

Ford et al, Fusion tails for the Recovery and Purification of Recombinant Proteins, Protein Expression and Purification, vol. 2: 95-107 (1991).
Porath et al., Metal chelate affinity chromatography, a new approach to protein fractionation, Nature 258:598-599 (1975).
Pedersen et al, Removal of N-Terminal Polyhistidine Tags from Recombinant Proteins Using Engineered Antibodies, Protein Expression and Purification, vol. 15: 389-400 (1999).
Colangeli et al., Three-step purificationof lipopolysaccaride-free, polyhistidine-tagged recombinant antigens of *Mycobacterium tuberculosis*, Journal of Chromatography B: Biomedical Sciences & Applications, vol. 714(2):223-235 (1998).
Larouche-Traineau et al., Three-step purification of bacterially expressed human single-chain Fv antibodies for clinical applications, Journal of Chromatography Biomedical Applications, vol. 737:107-117 (2000).
Porath et al., Immobilized Metal Ion Chromatography, Protein Expression and Purification, vol. 3: 263-281 (1992).

* cited by examiner

*Primary Examiner* — Elizabeth C Kemmerer
(74) *Attorney, Agent, or Firm* — Salvatore J. Arrigo; David C. Hoffman

(57) ABSTRACT

The present invention provides for a novel method for purification of EGFR family proteins obtained from cultures of insect cells. The process comprises subsequent steps of a) diafiltration and exchange of culture medium with buffer, b) immobilized metal affinity chromatography (IMAC), C) size exclusion chromatography (SEC), and d) anion exchange chromatography (AIE). The method also provides for an immunogenic variant of HER-2 protein which for which the purification process has been especially adapted, as well as means for the preparation of the variant.

6 Claims, 2 Drawing Sheets

SEQUENCE LISTING

```
<160> NUMBER OF SEQ ID NOS: 2

<210> SEQ ID NO 1
<211> LENGTH: 5661
<212> TYPE: DNA
<213> ORGANISM: Artificial sequence
<220> FEATURE:
<223> OTHER INFORMATION: Recombinant expression plasmid derived from pMT
<220> FEATURE:
<221> NAME/KEY: polyA_signal
<222> LOCATION: (263)..(268)
<223> OTHER INFORMATION: SV40 late polyadenylation site
<220> FEATURE:
<221> NAME/KEY: misc_feature
<222> LOCATION: (1579)..(2439)
<223> OTHER INFORMATION: Ampicillin resistance gene, encoded by
      complementary strand
<220> FEATURE:
<221> NAME/KEY: promoter
<222> LOCATION: (3050)..(3415)
<223> OTHER INFORMATION: Metallothionein promoter
<220> FEATURE:
<221> NAME/KEY: RBS
<222> LOCATION: (3493)..(3501)
<223> OTHER INFORMATION: Kozak-like sequence
<220> FEATURE:
<221> NAME/KEY: CDS
<222> LOCATION: (3502)..(5592)
<223> OTHER INFORMATION: DNA encoding immunogenic, his-tagged variant
      of human HER-2
<220> FEATURE:
<221> NAME/KEY: sig_peptide
<222> LOCATION: (3502)..(3555)
<223> OTHER INFORMATION: BiP signal sequence
<220> FEATURE:
<221> NAME/KEY: misc_feature
<222> LOCATION: (3556)..(3597)
<223> OTHER INFORMATION: Histidine tag
<220> FEATURE:
<221> NAME/KEY: mat_peptide
<222> LOCATION: (3556)..(5589)
<220> FEATURE:
<221> NAME/KEY: misc_feature
<222> LOCATION: (3598)..(3603)
<223> OTHER INFORMATION: Dipeptidase stop sequence
<220> FEATURE:
<221> NAME/KEY: misc_feature
<222> LOCATION: (3604)..(5589)
<223> OTHER INFORMATION: Gene coding for the hHER2MA5-5DUH protein
<220> FEATURE:
<221> NAME/KEY: misc_feature
<222> LOCATION: (4357)..(4401)
<223> OTHER INFORMATION: Diphtheria toxoid P2 epitope
<220> FEATURE:
<221> NAME/KEY: misc_feature
```

<222> LOCATION: (5500)..(5562)
<223> OTHER INFORMATION: Diphtheria toxoid P30 epitope

<400> SEQUENCE: 1
ggccgctcga gtctagaggg cccttcgaag gtaagcctat ccctaaccct ctcctcggtc 60
tcgattctac gcgtaccggt catcatcacc atcaccattg agtttaaacc cgctgatcag 120
cctcgactgt gccttctaag atccagacat gataagatac attgatgagt ttggacaaac 180
cacaactaga atgcagtgaa aaaaatgctt tatttgtgaa atttgtgatg ctattgcttt 240
atttgtaacc attataagct gcaataaaca agttaacaac aacaattgca ttcattttat 300
gtttcaggtt cagggggagg tgtgggaggt tttttaaagc aagtaaaacc tctacaaatg 360
tggtatggct gattatgatc agtcgacctg caggcatgca agcttggcgt aatcatggtc 420
atagctgttt cctgtgtgaa attgttatcc gctcacaatt ccacacaaca tacgagccgg 480
aagcataaag tgtaaagcct ggggtgccta atgagtgagc taactcacat taattgcgtt 540
gcgctcactg cccgctttcc agtcgggaaa cctgtcgtgc cagctgcatt aatgaatcgg 600
ccaacgcgcg gggagaggcg gtttgcgtat tgggcgctct tccgcttcct cgctcactga 660
ctcgctgcgc tcggtcgttc ggctgcggcg agcggtatca gctcactcaa aggcggtaat 720
acggttatcc acagaatcag gggataacgc aggaaagaac atgtgagcaa aaggccagca 780
aaaggccagg aaccgtaaaa aggccgcgtt gctggcgttt ttccataggc tccgcccccc 840
tgacgagcat cacaaaaatc gacgctcaag tcagaggtgg cgaaacccga caggactata 900
aagataccag gcgtttcccc ctggaagctc cctcgtgcgc tctcctgttc cgaccctgcc 960
gcttaccgga tacctgtccg cctttctccc ttcgggaagc gtggcgcttt ctcatagctc 1020
acgctgtagg tatctcagtt cggtgtaggt cgttcgctcc aagctgggct gtgtgcacga 1080
accccccgtt cagcccgacc gctgcgcctt atccggtaac tatcgtcttg agtccaaccc 1140
ggtaagacac gacttatcgc cactggcagc agccactggt aacaggatta gcagagcgag 1200
gtatgtaggc ggtgctacag agttcttgaa gtggtggcct aactacggct acactagaag 1260
gacagtattt ggtatctgcg ctctgctgaa gccagttacc ttcggaaaaa gagttggtag 1320
ctcttgatcc ggcaaacaaa ccaccgctgg tagcggtggt ttttttgttt gcaagcagca 1380
gattacgcgc agaaaaaaag gatctcaaga agatcctttg atcttttcta cggggtctga 1440
cgctcagtgg aacgaaaact cacgttaagg gattttggtc atgagattat caaaaaggat 1500
cttcacctag atccttttaa attaaaaatg aagttttaaa tcaatctaaa gtatatatga 1560
gtaaacttgg tctgacagtt accaatgctt aatcagtgag gcacctatct cagcgatctg 1620
tctatttcgt tcatccatag ttgcctgact ccccgtcgtg tagataacta cgatacggga 1680
gggcttacca tctggcccca gtgctgcaat gataccgcga gacccacgct caccggctcc 1740
agatttatca gcaataaacc agccagccgg aagggccgag cgcagaagtg gtcctgcaac 1800
tttatccgcc tccatccagt ctattaattg ttgccgggaa gctagagtaa gtagttcgcc 1860
agttaatagt ttgcgcaacg ttgttgccat tgctacaggc atcgtggtgt cacgctcgtc 1920
gtttggtatg gcttcattca gctccggttc ccaacgatca aggcgagtta catgatcccc 1980
catgttgtgc aaaaaagcgg ttagctcctt cggtcctccg atcgttgtca gaagtaagtt 2040
ggccgcagtg ttatcactca tggttatggc agcactgcat aattctctta ctgtcatgcc 2100
atccgtaaga tgcttttctg tgactggtga gtactcaacc aagtcattct gagaatagtg 2160
tatgcggcga ccgagttgct cttgcccggc gtcaatacgg gataataccg cgccacatag 2220
cagaacttta aaagtgctca tcattggaaa acgttcttcg gggcgaaaac tctcaaggat 2280

```
cttaccgctg ttgagatcca gttcgatgta acccactcgt gcacccaact gatcttcagc    2340 atctttact ttcaccagcg tttctgggtg agcaaaaaca ggaaggcaaa atgccgcaaa     2400
aaagggaata agggcgacac ggaaatgttg aatactcata ctcttccttt ttcaatatta    2460
ttgaagcatt tatcagggtt attgtctcat gagcggatac atatttgaat gtatttagaa    2520
aaataaacaa ataggggttc cgcgcacatt tccccgaaaa gtgccacctg acgtctaaga    2580
aaccattatt atcatgacat taacctataa aaataggcgt atcacgaggc cctttcgttc    2640
gcgcgtttcg gtgatgacgg tgaaaacctc tgacacatgc agctcccgga cgggtcaca    2700 gcttgtctgt aagcggatgc cgggagcaga caagcccgtc agggcgcgtc agcgggtgtt    2760
ggcgggtgtc ggggctggct taactatgcg gcatcagagc agattgtact gagagtgcac    2820
catatgcggt gtgaaatacc gcacagatgc gtaaggagaa ataccgcat caggcgccat     2880 tcgccattca ggctgcgcaa ctgttgggaa gggcgatcgg tgcgggcctc ttcgctatta    2940
cgccagctgg cgaaagggg atgtgctgca aggcgattaa gttgggtaac gccagggttt     3000
tcccagtcac gacgttgtaa aacgacggcc agtgccagtg aattaattcg ttgcaggaca    3060
ggatgtggtg cccgatgtga ctagctcttt gctgcaggcc gtcctatcct ctggttccga    3120
taagagaccc agaactccgg cccccaccg cccaccgcca ccccatacaa tatgtggtac       3180
gcaagtaaga gtgcctgcgc atgccccatg tgccccacca agagttttgc atcccataca    3240
agtccccaaa gtggagaacc gaaccaattc ttcgcgggca gaacaaaagc ttctgcacac    3300
gtctccactc gaatttggag ccggccgcg tgtgcaaaag aggtgaatcg aacgaaagac      3360
ccgtgtgtaa agccgcgttt ccaaaatgta taaaaccgag agcatctggc caatgtgcat    3420
cagttgtggt cagcagcaaa atcaagtgaa tcatctcagt gcaactaaag gggggatcta    3480
gatcggggta ccaaagtcac c atg aag ttg tgc atc ttg ctg gcc gtc gtg      3531
              Met Lys Leu Cys Ile Leu Leu Ala Val Val
                     -15                -10 gcc ttc gtg ggc ctg tcg ctg ggc atg aag cac caa cac caa cat caa      3579
Ala Phe Val Gly Leu Ser Leu Gly Met Lys His Gln His Gln His Gln
         -5               -1  1                 5 cat caa cat caa cat caa gcc ccc tcc acc caa gtg tgt acc ggc aca      3627
His Gln His Gln His Gln Ala Pro Ser Thr Gln Val Cys Thr Gly Thr
    10              15                  20 gac atg aag ctg cgg ctc cct gcc agt ccc gag acc cac ctg gac atg      3675
Asp Met Lys Leu Arg Leu Pro Ala Ser Pro Glu Thr His Leu Asp Met
25              30                  35                  40 ctc cgc cac ctc tac cag ggc tgc cag gtg gtg cag gga aac ctg gaa      3723
Leu Arg His Leu Tyr Gln Gly Cys Gln Val Val Gln Gly Asn Leu Glu
             45                  50                  55 ctc acc tac ctg ccc acc aat gcc agc tta agt ttc ctg cag gat atc      3771
Leu Thr Tyr Leu Pro Thr Asn Ala Ser Leu Ser Phe Leu Gln Asp Ile
         60                  65                  70 cag gag gtg cag ggc tac gtg ctc atc gct cac aac caa gtg agg cag      3819
Gln Glu Val Gln Gly Tyr Val Leu Ile Ala His Asn Gln Val Arg Gln
             75                  80                  85 gtc cca ctg cag agg ctg cgg att gtg cga ggc acc cag ctc ttt gag      3867
Val Pro Leu Gln Arg Leu Arg Ile Val Arg Gly Thr Gln Leu Phe Glu
     90                  95                  100 gac aac tat gcc ctg gcc gtg cta gac aat gga gac ccg ctg aac aat      3915
Asp Asn Tyr Ala Leu Ala Val Leu Asp Asn Gly Asp Pro Leu Asn Asn
105                 110                 115                 120 acc acc cct gtc aca ggg gcc tcc cca gga ggc ctg cgg gag ctg cag      3963
Thr Thr Pro Val Thr Gly Ala Ser Pro Gly Gly Leu Arg Glu Leu Gln
                125                 130                 135
```

```
ctt cga agc ctc aca gag atc ttg aaa gga ggg gtc ttg atc cag cgg     4011
Leu Arg Ser Leu Thr Glu Ile Leu Lys Gly Gly Val Leu Ile Gln Arg
        140                 145                 150 aac ccc cag ctc tgc tac cag gac acg att ttg tgg aag gac atc ttc     4059
Asn Pro Gln Leu Cys Tyr Gln Asp Thr Ile Leu Trp Lys Asp Ile Phe
    155                 160                 165 cac aag aac aac cag ctg gct ctc aca ctg ata gac acc aac cgc tct     4107
His Lys Asn Asn Gln Leu Ala Leu Thr Leu Ile Asp Thr Asn Arg Ser
170                 175                 180 cgg gcc tgc cac ccc tgt tct ccg atg tgt aag ggc tcc cgc tgc tgg     4155
Arg Ala Cys His Pro Cys Ser Pro Met Cys Lys Gly Ser Arg Cys Trp
185                 190                 195                 200 gga gag agt tct gag gat tgt cag agc ctg acg cgc act gtc tgt gcc     4203
Gly Glu Ser Ser Glu Asp Cys Gln Ser Leu Thr Arg Thr Val Cys Ala
            205                 210                 215 ggt ggc tgt gcc cgc tgc aag ggg cca ctg ccc act gac tgc tgc cat     4251
Gly Gly Cys Ala Arg Cys Lys Gly Pro Leu Pro Thr Asp Cys Cys His
        220                 225                 230 gag cag tgt gct gcc ggc tgc acg ggc ccc aag cac tct gac tgc ctg     4299
Glu Gln Cys Ala Ala Gly Cys Thr Gly Pro Lys His Ser Asp Cys Leu
    235                 240                 245 gcc tgc ctc cac ttc aac cac agt ggc atc tgt gag ctg cac tgc cca     4347
Ala Cys Leu His Phe Asn His Ser Gly Ile Cys Glu Leu His Cys Pro
250                 255                 260 gcc ctg gtc cag tac atc aaa gct aac tcc aaa ttc atc ggt atc acc     4395
Ala Leu Val Gln Tyr Ile Lys Ala Asn Ser Lys Phe Ile Gly Ile Thr
265                 270                 275                 280 gag ctg cgg tat aca ttc ggc gcc agc tgt gtg act gcc tgt ccc tac     4443
Glu Leu Arg Tyr Thr Phe Gly Ala Ser Cys Val Thr Ala Cys Pro Tyr
            285                 290                 295 aac tac ctt tct acg gac gtg gga tcc tgc acc ctc gtc tgc ccc ctg     4491
Asn Tyr Leu Ser Thr Asp Val Gly Ser Cys Thr Leu Val Cys Pro Leu
        300                 305                 310 cac aac caa gag gtg aca gca gag gat gga aca cag cgg tgt gag aag     4539
His Asn Gln Glu Val Thr Ala Glu Asp Gly Thr Gln Arg Cys Glu Lys
    315                 320                 325 tgc agc aag ccc tgt gcc cga gtg tgc tat ggt ctg ggc atg gag cac     4587
Cys Ser Lys Pro Cys Ala Arg Val Cys Tyr Gly Leu Gly Met Glu His
330                 335                 340 ttg cga gag gtg agg gca gtt acc agt gcc aat atc cag gag ttt gct     4635
Leu Arg Glu Val Arg Ala Val Thr Ser Ala Asn Ile Gln Glu Phe Ala
345                 350                 355                 360 ggc tgc aag aag atc ttt ggg agc ctg gca ttt ctg ccg gag agc ttt     4683
Gly Cys Lys Lys Ile Phe Gly Ser Leu Ala Phe Leu Pro Glu Ser Phe
            365                 370                 375 gat ggg gac cca gcc tcc aac act gcc ccg ctc cag cca gag cag ctc     4731
Asp Gly Asp Pro Ala Ser Asn Thr Ala Pro Leu Gln Pro Glu Gln Leu
        380                 385                 390 caa gtg ttt gag act ctg gaa gag atc aca ggt tac cta tac atc tca     4779
Gln Val Phe Glu Thr Leu Glu Glu Ile Thr Gly Tyr Leu Tyr Ile Ser
    395                 400                 405 gca tgg ccg gac agc ctg cct gac ctc agc gtc ttc cag aac ctg caa     4827
Ala Trp Pro Asp Ser Leu Pro Asp Leu Ser Val Phe Gln Asn Leu Gln
410                 415                 420 gta atc cgg gga cga att ctg cac aat ggc gcc tac tcg ctg acc ctg     4875
Val Ile Arg Gly Arg Ile Leu His Asn Gly Ala Tyr Ser Leu Thr Leu
425                 430                 435                 440 caa ggg ctg ggc atc agc tgg ctg ggg ctg cgc tca ctg agg gaa ctg     4923
Gln Gly Leu Gly Ile Ser Trp Leu Gly Leu Arg Ser Leu Arg Glu Leu
            445                 450                 455
```

```
ggc agt gga ctg gcc ctc atc cac cat aac acc cac ctc tgc ttc gtg        4971
Gly Ser Gly Leu Ala Leu Ile His His Asn Thr His Leu Cys Phe Val
            460                 465                 470 cac acg gtg ccc tgg gac cag ctc ttt cgg aac ccg cac caa gct ctg        5019
His Thr Val Pro Trp Asp Gln Leu Phe Arg Asn Pro His Gln Ala Leu
            475                 480                 485 ctc cac act gcc aac cgg cca gag gac gag tgt gtg ggc gag ggc ctg        5067
Leu His Thr Ala Asn Arg Pro Glu Asp Glu Cys Val Gly Glu Gly Leu
490                 495                 500 gcc tgc cac cag ctg tgc gcc cga ggg cac tgc tgg ggt cca ggg ccc        5115
Ala Cys His Gln Leu Cys Ala Arg Gly His Cys Trp Gly Pro Gly Pro
505                 510                 515                 520 acc cag tgt gtc aac tgc agc cag ttc ctt cgg ggc cag gag tgc gtg        5163
Thr Gln Cys Val Asn Cys Ser Gln Phe Leu Arg Gly Gln Glu Cys Val
            525                 530                 535 gag gaa tgc cga gta ctg cag ggg ctc ccc agg gag tat gtg aat gcc        5211
Glu Glu Cys Arg Val Leu Gln Gly Leu Pro Arg Glu Tyr Val Asn Ala
            540                 545                 550 agg cac tgt ttg ccg tgc cac cct gag tgt cag ccc cag aat ggc tca        5259
Arg His Cys Leu Pro Cys His Pro Glu Cys Gln Pro Gln Asn Gly Ser
            555                 560                 565 gtg acc tgt ttt gga ccg gag gct gac cag tgt gtg gcc tgt gcc cac        5307
Val Thr Cys Phe Gly Pro Glu Ala Asp Gln Cys Val Ala Cys Ala His
570                 575                 580 tat aag gac cct ccc ttc tgc gtg gcc cgc tgc ccc agc ggt gtg aaa        5355
Tyr Lys Asp Pro Pro Phe Cys Val Ala Arg Cys Pro Ser Gly Val Lys
585                 590                 595                 600 cct gac ctc tcc tac atg ccc atc tgg aag ttt cca gat gag gag ggc        5403
Pro Asp Leu Ser Tyr Met Pro Ile Trp Lys Phe Pro Asp Glu Glu Gly
            605                 610                 615 gca tgc cag cct tgc ccc atc aac tgc acc cac tcc tgt gtg gac ctg        5451
Ala Cys Gln Pro Cys Pro Ile Asn Cys Thr His Ser Cys Val Asp Leu
            620                 625                 630 gat gac aag ggc tgc ccc gcc gag cag aga gcc agc cct ctg acg tcc        5499
Asp Asp Lys Gly Cys Pro Ala Glu Gln Arg Ala Ser Pro Leu Thr Ser
            635                 640                 645 ttc aac aac ttc acc gtg agc ttc tgg ctg cgc gtg ccc aag gtg agc        5547
Phe Asn Asn Phe Thr Val Ser Phe Trp Leu Arg Val Pro Lys Val Ser
650                 655                 660 gcc agc cac ctg gag atc gtc tct gcg gtg gtt ggc att ctg                5589
Ala Ser His Leu Glu Ile Val Ser Ala Val Val Gly Ile Leu
665                 670                 675 tagaagcttg gtaccgagct cggatccact agtccagtgt ggtggaattc tgcagatatc     5649
cagcacagtg gc                                                          5661

<210> SEQ ID NO 2
<211> LENGTH: 696
<212> TYPE: PRT
<213> ORGANISM: Artificial sequence
<220> FEATURE:
<223> OTHER INFORMATION: Recombinant expression plasmid derived from pSI

<400> SEQUENCE: 2

Met Lys Leu Cys Ile Leu Leu Ala Val Val Ala Phe Val Gly Leu Ser
            -15                 -10                 -5

Leu Gly Met Lys His Gln His Gln His Gln His Gln His Gln His Gln
 -1  1              5                   10

Ala Pro Ser Thr Gln Val Cys Thr Gly Thr Asp Met Lys Leu Arg Leu
15                  20                  25                  30
```

```
Pro Ala Ser Pro Glu Thr His Leu Asp Met Leu Arg His Leu Tyr Gln
            35                  40                  45
Gly Cys Gln Val Val Gln Asn Leu Glu Leu Thr Tyr Leu Pro Thr
            50                  55                  60
Asn Ala Ser Leu Ser Phe Leu Gln Asp Ile Gln Glu Val Gln Gly Tyr
            65                  70                  75
Val Leu Ile Ala His Asn Gln Val Arg Gln Val Pro Leu Gln Arg Leu
    80                  85                  90
Arg Ile Val Arg Gly Thr Gln Leu Phe Glu Asp Asn Tyr Ala Leu Ala
95                  100                 105                 110
Val Leu Asp Asn Gly Asp Pro Leu Asn Asn Thr Thr Pro Val Thr Gly
            115                 120                 125
Ala Ser Pro Gly Gly Leu Arg Glu Leu Gln Leu Arg Ser Leu Thr Glu
            130                 135                 140
Ile Leu Lys Gly Gly Val Leu Ile Gln Arg Asn Pro Gln Leu Cys Tyr
            145                 150                 155
Gln Asp Thr Ile Leu Trp Lys Asp Ile Phe His Lys Asn Asn Gln Leu
            160                 165                 170
Ala Leu Thr Leu Ile Asp Thr Asn Arg Ser Arg Ala Cys His Pro Cys
175                 180                 185                 190
Ser Pro Met Cys Lys Gly Ser Arg Cys Trp Gly Glu Ser Ser Glu Asp
            195                 200                 205
Cys Gln Ser Leu Thr Arg Thr Val Cys Ala Gly Gly Cys Ala Arg Cys
            210                 215                 220
Lys Gly Pro Leu Pro Thr Asp Cys Cys His Glu Gln Cys Ala Ala Gly
            225                 230                 235
Cys Thr Gly Pro Lys His Ser Asp Cys Leu Ala Cys Leu His Phe Asn
240                 245                 250
His Ser Gly Ile Cys Glu Leu His Cys Pro Ala Leu Val Gln Tyr Ile
255                 260                 265                 270
Lys Ala Asn Ser Lys Phe Ile Gly Ile Thr Glu Leu Arg Tyr Thr Phe
            275                 280                 285
Gly Ala Ser Cys Val Thr Ala Cys Pro Tyr Asn Tyr Leu Ser Thr Asp
            290                 295                 300
Val Gly Ser Cys Thr Leu Val Cys Pro Leu His Asn Gln Glu Val Thr
            305                 310                 315
Ala Glu Asp Gly Thr Gln Arg Cys Glu Lys Cys Ser Lys Pro Cys Ala
            320                 325                 330
Arg Val Cys Tyr Gly Leu Gly Met Glu His Leu Arg Glu Val Arg Ala
335                 340                 345                 350
Val Thr Ser Ala Asn Ile Gln Glu Phe Ala Gly Cys Lys Lys Ile Phe
            355                 360                 365
Gly Ser Leu Ala Phe Leu Pro Glu Ser Phe Asp Gly Asp Pro Ala Ser
            370                 375                 380
Asn Thr Ala Pro Leu Gln Pro Glu Gln Leu Gln Val Phe Glu Thr Leu
            385                 390                 395
Glu Glu Ile Thr Gly Tyr Leu Tyr Ile Ser Ala Trp Pro Asp Ser Leu
            400                 405                 410
Pro Asp Leu Ser Val Phe Gln Asn Leu Gln Val Ile Arg Gly Arg Ile
415                 420                 425                 430
Leu His Asn Gly Ala Tyr Ser Leu Thr Leu Gln Gly Leu Gly Ile Ser
            435                 440                 445
Trp Leu Gly Leu Arg Ser Leu Arg Glu Leu Gly Ser Gly Leu Ala Leu
            450                 455                 460
```

```
Ile His His Asn Thr His Leu Cys Phe Val His Thr Val Pro Trp Asp
        465             470             475

Gln Leu Phe Arg Asn Pro His Gln Ala Leu Leu His Thr Ala Asn Arg
    480             485             490

Pro Glu Asp Glu Cys Val Gly Glu Gly Leu Ala Cys His Gln Leu Cys
495             500             505                         510

Ala Arg Gly His Cys Trp Gly Pro Gly Pro Thr Gln Cys Val Asn Cys
            515             520                     525

Ser Gln Phe Leu Arg Gly Gln Glu Cys Val Glu Glu Cys Arg Val Leu
            530             535             540

Gln Gly Leu Pro Arg Glu Tyr Val Asn Ala Arg His Cys Leu Pro Cys
        545             550             555

His Pro Glu Cys Gln Pro Gln Asn Gly Ser Val Thr Cys Phe Gly Pro
        560             565             570

Glu Ala Asp Gln Cys Val Ala Cys Ala His Tyr Lys Asp Pro Pro Phe
575             580             585                         590

Cys Val Ala Arg Cys Pro Ser Gly Val Lys Pro Asp Leu Ser Tyr Met
            595             600             605

Pro Ile Trp Lys Phe Pro Asp Glu Glu Gly Ala Cys Gln Pro Cys Pro
            610             615             620

Ile Asn Cys Thr His Ser Cys Val Asp Leu Asp Asp Lys Gly Cys Pro
        625             630             635

Ala Glu Gln Arg Ala Ser Pro Leu Thr Ser Phe Asn Asn Phe Thr Val
        640             645             650

Ser Phe Trp Leu Arg Val Pro Lys Val Ser Ala Ser His Leu Glu Ile
655             660             665                         670

Val Ser Ala Val Val Gly Ile Leu
                675
```

IMMUNOGENIC HER-2 VARIANTS

CROSS-REFERENCE TO RELATED APPLICATIONS

Figure 1:
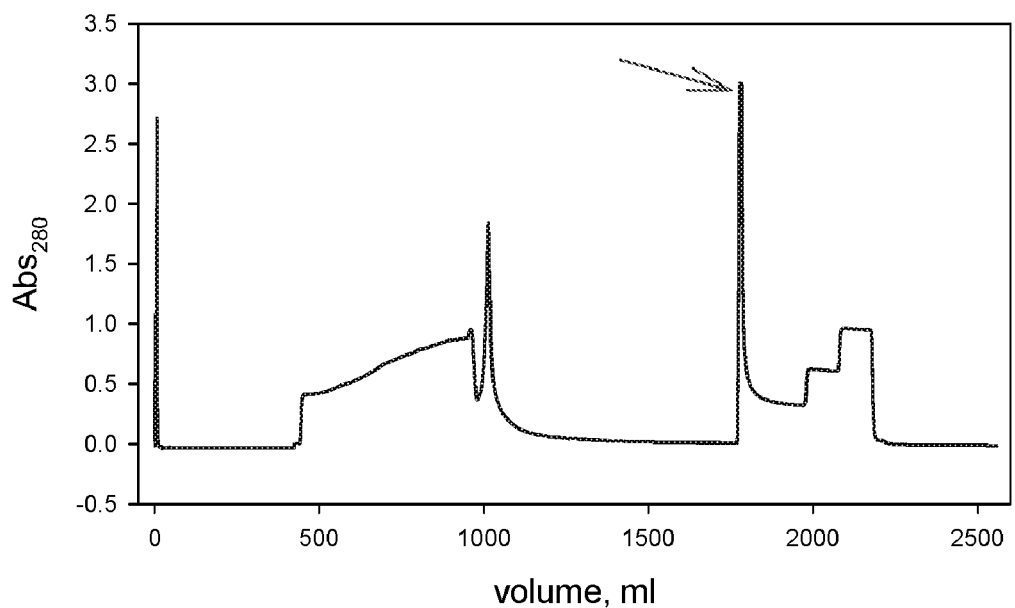

This is a divisional of U.S. application Ser. No. 10/560,961, filed May 30, 2006, now U.S. Pat. No. 7,763,452 B2, which is the U.S. National Stage of International Application No. PCT/DK2004/000451, filed Jun. 24, 2004, which claims the benefit of Danish Application No. PA 2003 00954, filed Jun. 25, 2003, and U.S. Provisional Application No. 60/482,315, filed Jun. 25, 2003, all of which are hereby incorporated herein by reference.

FIELD OF THE INVENTION

The present invention relates to the field of affinity purification of proteins. More particularly, the present invention relates to improvements in metal affinity protein purification, especially purification of histidine tagged or histidine rich proteins that have been recombinantly produced in insect cells. The invention also relates to specific purification schemes suitable for histidine-tagged protein variants derived from the EGFR (endothelial growth factor receptor) family of proteins, especially the cancer-associated antigen HER-2.

Further, the present invention relates to an immunogenic variant of human HER-2 that is capable of raising an immune response in humans, which also targets the native human HER-2 molecule.

BACKGROUND OF THE INVENTION

The cancer associated membrane protein HER-2 is a member of the EGFR family of proteins. This particular protein has shown promise as an immunogen in active specific immunotherapy of certain cancers, notably breast cancer and colorectal cancer.

The assignee of the present patent application has previously filed patent applications relating to active vaccination against the HER-2 antigen, cf. WO 00/20027 which is hereby incorporated by reference herein. Further research in this field has now identified preferred HER-2 variants for such vaccines, but a general problem in protein chemistry is to devise improved means for obtaining satisfactory yields of recombinant protein with a high degree of purity.

Immobilized metal ion affinity chromatography (IMAC) was first introduced by Porath (Porath, J., J. Carlsson, I. Olsson, G. Belfrage [1975] Nature 258:598-599.) under the term metal chelate chromatography and has been previously reviewed in several articles (Porath, J. [1992] Protein Purification and Expression 3:263-281; and articles cited therein). The IMAC purification process is based on the employment of a chelating matrix loaded with soft metal ions such as $Cu^{2+}$ and $Ni^{2+}$. Electron-donating groups on the surface of proteins, especially the imidazole side chain of histidine, can bind to the non-coordinated sites of the loaded metal. The interaction between the electron donor group with the metal can be made reversible by lowering the pH or by displacement with imidazole. Thus, a protein possessing electron-donating groups such as histidine can be purified by reversible metal complex/protein interactions.

In 1991, Ford et al. (Ford, C., I. Suominen, C. Glatz [1991] Protein Expression and Purification 2:95-107) described protein purification using IMAC technology (Ni-NTA ligand) as applied to recombinant proteins having tails with histidine residues (polyhistidine recombinant proteins, "His-tagged proteins"). This method takes advantage of the fact that two or more histidine residues can cooperate to form very strong metal ion complexes.

Numerous variations of this technology exists, where the histidine residues are attached as "tags" to the relevant recombinant protein in various combinations, e.g. including recognition sites for specific proteases so that the his tag can be subsequently removed enzymatically.

Expression of proteins in insect cells require the use of various specialised culture media and also entails contamination of the recombinant protein with various insect cell derived constituents that are not found in bacteria, fungi and mammalian cells. Purification schemes devised for recombinant proteins produced in bacteria, fungi, or mammalian cells are therefore not necessarily the optimum choice when a protein produced in insect cells will need to be purified.

There is therefore a continuing need for improvements in protein purification in order to obtain pharmaceutical grade protein derived from recombinant production in insect cells.

OBJECT OF THE INVENTION

It is an object of the invention to provide an improved method for purifying recombinant EGFR family protein expressed in insect cells. It is a further object of the invention to provide an immunogenic variant of HER-2 protein that is useful in e.g. cancer treatment by means of specific active immunotherapy.

SUMMARY OF THE INVENTION

The present inventors have devised a novel method for purifying EGFR family protein to a degree of purity, which is acceptable for pharmaceutical use, notably for use as vaccine agents.

Hence, in one aspect, the present invention relates to a method for purification of an EGFR family derived protein, said protein being recombinantly produced in an insect cell culture and said protein being one that is suitable for purification by means of immobilised metal affinity chromatography, the method comprising obtaining, from said insect cell culture, a substantially cell-free sample containing said EGFR family derived protein, and thereafter enriching for said EGFR family derived protein by means of subsequent steps of:

diafiltration and exchange of culture medium with buffer,
immobilized metal affinity chromatography (IMAC),
size exclusion chromatography (SEC), and
anion exchange chromatography (AIE).

Another aspect of the invention relates to an immunogenic variant of HER-2 protein that comprises the amino acid sequence set forth in SEQ ID NO: 2, residues 17-677.

LEGENDS TO THE FIGURE

Figure 2:
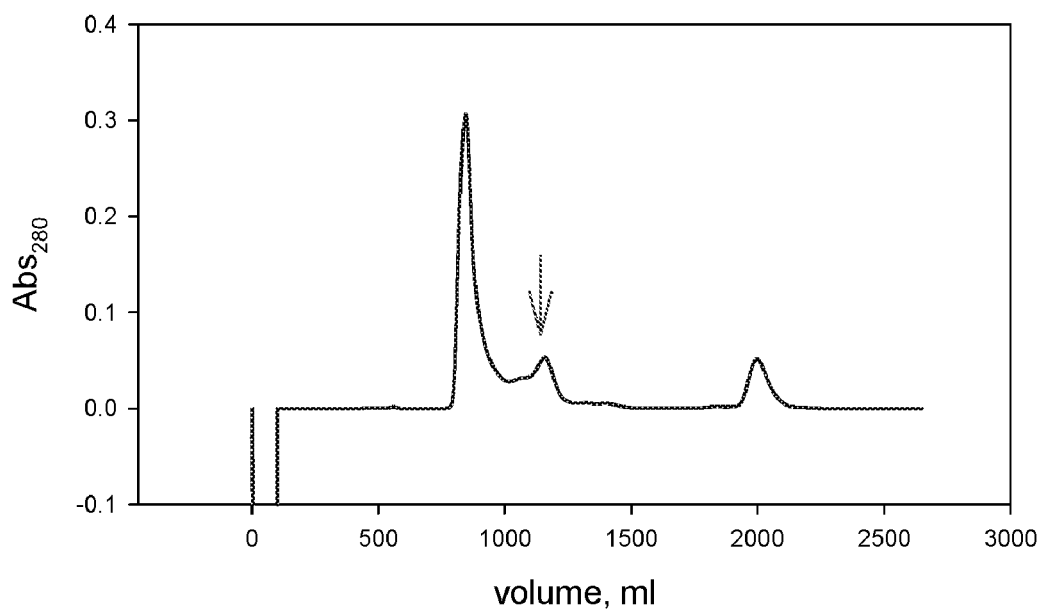
Figure 3:
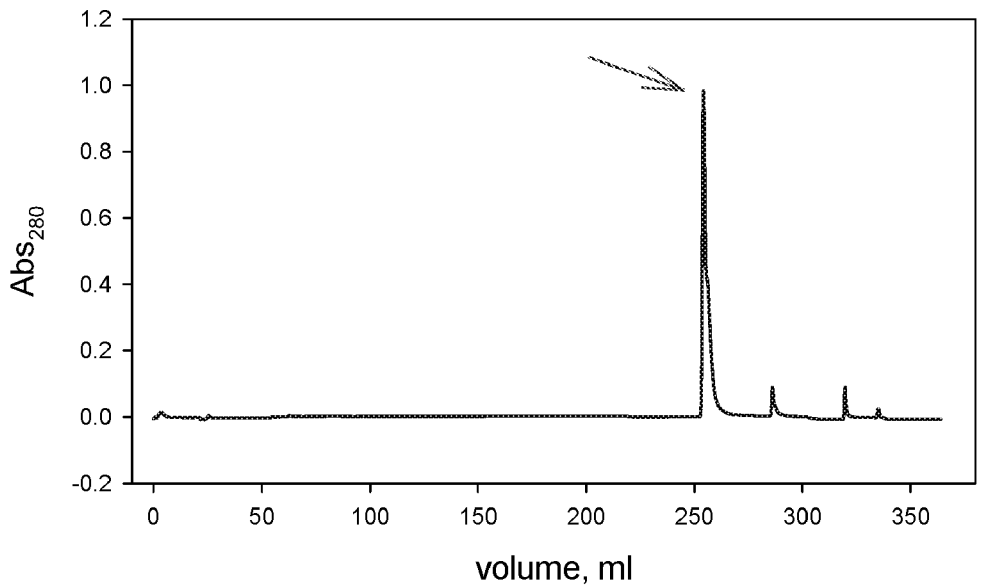
Figure 4:
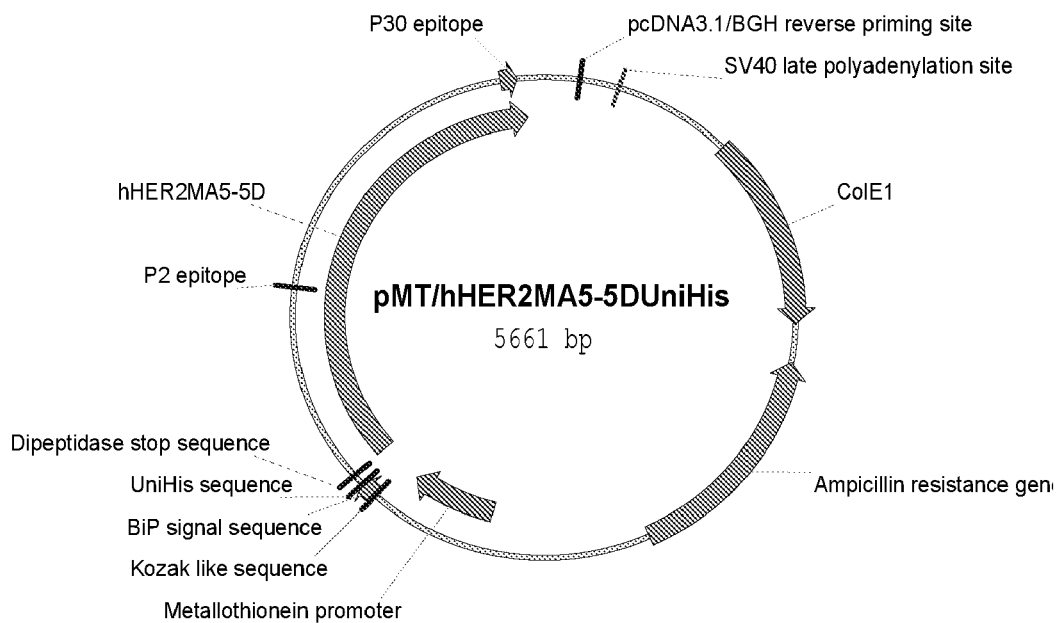

FIG. 1: Chromatographic profile of the IMAC.
The arrow indicates the 104.1 peak.
FIG. 2: Chromatographic profile of the SEC.
The arrow indicates the monomer peak.
FIG. 3: Chromatographic profile of the AIE.
The arrow indicates the 104.1 peak.
FIG. 4: The pMT/hHER2MA5-5DUniHis vector p992, plasmid map.
hHER2MA5-5D: Gene coding for the hHER2MA5-5DUH protein (nucleotides 3604-5592).
P2 epitope: Sequence coding for the P2 epitope in the hHER2MA5-5DUH protein (nucleotides 4357-4401).

P30 epitope: Sequence coding for the P30 epitope in the hHER2MA5-5DUH protein (nucleotides 5500-5562).

SV40 late Polyadenylation site: Poly A signal (nucleotides 263-268).

ColE1: Origin of replication for replication in *E. coli* (nucleotides 701-1434).

Ampicillin resistance gene: Gene conferring ampicillin resistance in bacteria (nucleotides 1579-2439).

Metallothionein promoter: Promoter that can be induced with a number of compounds (e.g. cadmium) (nucleotides 3050-3415).

Kozak like sequence: Ribosomal binding site (nucleotides 3493-3501).

BiP signal sequence: Signal sequence directing the HER2 variant protein to secretion into the extracellular compartment (nucleotides 3502-3555).

UniHis sequence: Sequence coding for the UniHis tag used for purification of the HER2 AutoVac protein (nucleotides 3556-3597).

Dipeptidase stop sequence: Used if the UniHis tag is to be cleaved from the HER2 AutoVac protein (nucleotides 3598-3603).

DETAILED DISCLOSURE OF THE INVENTION

In the following a number of terms and expressions will be defined in the context of the present invention.

"An EGFR family derived protein" denotes a protein which is homologous to or identical with human EGFR (or ErbB-1); human HER-2/neu (ErbB-2); HER-3 (ErbB-3); or HER-4 (ErbB-4).

An "autologous" EGFR family protein is in the present specification and claims intended to denote an EGFR family polypeptide of an animal that is going to be vaccinated against its own EGFR family protein. In other words, the term is only relevant when the relation to the animal that it going to be vaccinated is considered.

The terms "T-lymphocyte" and "T-cell" will be used interchangeably for lymphocytes of thymic origin which are responsible for various cell mediated immune responses as well as for effector functions such as helper activity in the humeral immune response. Likewise, the terms "B-lymphocyte" and "B-cell" will be used interchangeably for antibody-producing lymphocytes.

An "antigen presenting cell" (APC) is a cell which presents epitopes to T-cells. Typical antigen-presenting cells are macrophages, dendritic cells and other phagocytizing and pinocytizing cells. It should be noted that B-cells also functions as APCs by presenting $T_H$ epitopes bound to MCH class II molecules to $T_H$ cells but when generally using the term APC in the present specification and claims it is intended to refer to the above-mentioned phagocytizing and pinocytizing cells.

"Helper T-lymphocytes" or "$T_H$ cells" denotes CD4 positive T-cells, which provide help to B-cells and cytotoxic T-cells via the recognition of $T_H$ epitopes bound to MHC Class II molecules on antigen presenting cells.

The term "cytotoxic T-lymphocyte" (CTL) will be used for CD8 positive T-cells, which require the assistance of $T_H$ cells in order to become activated.

A "specific" immune response is in the present context intended to denote a polyclonal immune response directed predominantly against a molecule or a group of quasi-identical molecules or, alternatively, against cells which present CTL epitopes of the molecule or the group of quasi-identical molecules.

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide(s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively.

By the term "down-regulation an autologous EGFR family protein" is herein meant reduction in the living organism of the amount and/or activity of the relevant EGFR family protein. The down-regulation can be obtained by means of several mechanisms including removal of the CEA by scavenger cells (such as macrophages and other phagocytizing cells), and even more important, that cells carrying or harbouring the antigen are killed by CTLs in the animal.

The term "immunogen" is intended to denote a substance capable of inducing an immune response in a certain animal. It will therefore be understood that an autologous EGFR family protein is not an immunogen in the autologous host—it is necessary to use either a strong adjuvant and/or to co-present T helper epitopes with the autologous protein in order to mount an immune response against autologous protein and in such a case the "immunogen" is the composition of matter which is capable of breaking autotolerance.

The term "immunogenically effective amount" has its usual meaning in the art, i.e. an amount of an immunogen, which is capable of inducing an immune response, which significantly engages pathogenic agents, which share immunological features with the immunogen.

The term "pharmaceutically acceptable" has its usual meaning in the art, i.e. it is used for a substance that can be accepted as part of a medicament for human use when treating the disease in question and thus the term effectively excludes the use of highly toxic substances that would worsen rather than improve the treated subject's condition.

A "foreign T-cell epitope" is a peptide which is able to bind to an MHC molecule and which stimulates T-cells in an animal species. Preferred foreign epitopes are "promiscuous" epitopes, i.e. epitopes, which binds to a substantial fraction of MHC class II molecules in an animal species or population. A term, which is often used interchangeably in the art, is the term "universal T-cell epitopes" for this kind of epitopes. Only a very limited number of such promiscuous T-cell epitopes are known, and they will be discussed in detail below. It should be noted that in order for the immunogens which are used according to the present invention to be effective in as large a fraction of an animal population as possible, it may be necessary to 1) insert several foreign T-cell epitopes in the same analogue or 2) prepare several analogues wherein each analogue has a different promiscuous epitope inserted. It should be noted that the concept of foreign T-cell epitopes also encompasses use of cryptic T-cell epitopes, i.e. epitopes which are derived from a self-protein and which only exerts immunogenic behaviour when existing in isolated form without being part of the self-protein in question.

A "foreign T helper lymphocyte epitope" (a foreign $T_H$ epitope) is a foreign T cell epitope, which binds an MHC Class II molecule and can be presented on the surface of an antigen presenting cell (APC) bound to the MHC Class II molecule. It is also important to add that the "foreignness" feature therefore has two aspects: A foreign $T_H$ epitope is 1) presented in the MHC Class II context by the animal in question and 2) the foreign epitope is not derived from the same polypeptide as the target antigen for the immunization—the epitope is thus also foreign to the target antigen.

A "CTL epitope" is a peptide, which is able to bind to an MHC class I molecule.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Diafiltration" is a technique using ultrafiltration membranes to remove salt or solvent, exchange buffers, or fractionate different size biomolecules in macromolecular solutions. Macromolecules retained by the ultrafiltration membrane are concentrated while solvent and lower molecular weight species are removed. However, a simple concentration of the macromolecular sample will not completely remove the smaller species. Therefore, the smaller species must be "washed" from the sample using multiple wash volumes (diafiltration). After the diafiltration process, the sample can be concentrated for further analysis or purification. This is an advantage compared with gel filtration or dialysis when the sample can be diluted during the separation process, requiring an additional concentration step. There is no loss or contamination using diafiltration as could occur with a two-step process.

"Immobilised metal affinity chromatography" (IMAC) is a chromatographic technique where proteins are purified as a consequence of their affinity for certain divalent metal ions, cf. the description in the "Background of the Invention".

"Size exclusion chromatography" (SEC) is a chromatographic technique, where proteins and other macromolecules are fractionated according to their physical size. Small molecules are retained in pores of the matrix and are therefore eluted slowly, whereas larger molecules are excluded and therefore eluted early from the matrix.

"Anion Exchange Chromatography" (AIE) is a chromatographic technique, where molecules having a net negative charge are retained on the column matrix and subsequently eluted by displacing with anion from the elution buffer or by changing net charge of the protein.

DESCRIPTION OF THE PREFERRED EMBODIMENTS

The present invention relates to a purification process that is especially tailored for purification of EGFR family derived proteins that have been produced recombinantly in insect cells. The present invention was conceived in connection with efforts that have led to the preparation of immunogenic variants of the human cancer-associated antigen HER-2—these variants are produced in the DES® expression system, an expression system owned by GlaxoSmithKline and marketed by i.a. Invitrogen. The system utilises S2 Drosophila cells and specialised vectors. The use of S2 cells as host cells for recombinant production has, however, posed its own set of problems to solve vis-à-vis the HER-2 variant in question, and these problems have been solved by using the inventive method (i.a. problems with co-migrating proteins which are derived from the S2 cells).

The particular protein that is used in the Examples is a variant of human HER-2, which is immunogenic in humans—the variant includes the amino acid sequence set forth in SEQ ID NO: 2, residues 17-677. However, since this amino acid sequence is not in itself suitable for IMAC, it contains an N-terminal histidine tag (amino acid residues 1-14 in SEQ ID NO: 1) that can be cleaved off by an aminodipeptidase (dipeptidyl peptidase I, DPPI, cf. Pedersen J et al., 1999, Protein Expression and Purification 15, 389-400). The stop sequence for the diaminopeptidase consists of residues 15 and 16 in SEQ ID NO: 2.

Therefore, in general the instant purification method is especially suited for EGFR family derived proteins that include a heterologous amino acid sequence that facilitates purification by means of IMAC. This sequence may be native to the EGFR family derived protein, but more often it is heterologous amino acid sequence (i.e. not naturally associated with the EGFR family derived protein). Preferred amino acid sequences for this purpose are rich in histidine residues (e.g. the $His_6$ tag and other amino acid sequences with several consecutive histidine residues). The most preferred heterologous amino acid sequence that facilitates IMAC purification is the one comprising residues 1-14 of SEQ ID NO: 2.

The EGFR derived protein subjected to the inventive process is preferably one that comprises a substantial part of the amino acid sequence of human EGFR or human HER-2, and it is especially preferred the this substantial part is mainly derived from the extracellular portion of human EGFR or human HER-2. Most preferred is a variant of human HER-2, and in the most preferred embodiments, the variant of human HER-2 includes at least one foreign T helper cell epitope.

As mentioned above, the inventive process has been conceived in connection with work on recombinant production of certain variants of human HER-2 antigen. These variants are characteristic in including promiscuous foreign T-helper epitopes that are introduced into the amino acid sequence of human HER-2 extracellular domain. Preferred variants of human HER-2 include tetanus toxoid epitopes P2 (residues 269-282 of SEQ ID NO: 2) and P30 (residues 649-669 of SEQ ID NO: 2) and the most preferred variant has an amino acid sequence that consists of residues 1-677 of SEQ ID NO: 2

Diafiltration/Buffer Exchange

The step of diafiltration/buffer exchange is performed at a temperature from about 2 to about 25° C. However, preferably temperatures in the lower part of the range are used, e.g. temperatures below 20° C., such as below 15° C. or below 10° C. Most preferred temperatures are in the range between 2 and 9° C., such as in the range between about 3° C. and about 9° C., with a most preferred temperature range from about 3 to about 8 and especially preferred from 4 to about 6° C. At higher temperatures (e.g. beyond 10° C.) there is a tendency that the protein aggregates, and this can be counteracted by adding a detergent, such as a Tween type detergent.

Normally, the diafiltration is performed in two rounds so as to initially concentrate macromolecular compounds in the sample of culture medium and thereafter to exchange culture medium with buffer. These procedures are done following standard procedures in the art, cf. also the examples. It is preferred that the concentration step results in a concentration of between 2 and 25 times of the macromolecular compounds, such as a concentration between 2 and 20 times, 3 and 15 times, between 3 and 10 times. Preferred concentration of macromolecular compounds is in the range of between 4 and 8 times, and the most preferred concentration is about 5 times or to a total protein concentration of the medium not exceeding 3 mg/ml, or preferably not exceeding 2 mg/ml.

The buffer exchange is typically performed in two subsequent steps of which the first takes place at a pH of at least 6.5 and at most 7.2 and of which the second takes place at a pH of at least 7.0 and of most 8.0. It is, however, possible to perform both steps at the same pH in the overlapping part of the two ranges. Typically, the buffer exchange is performed using a phosphate buffer.

After completion of the buffer exchange, the stringency of the following steps is preferably increased by adding an agent to the sample that will compete for binding to the chromatographic matrix in the IMAC step so as to reduce the amount of non-significant binding by contaminating constituents. For example, addition of imidazole, histidine or a high salt concentration buffer to the diafiltrated and buffer can be done to increase the stringency. Preferably, when imidazole is used, it is added so as to reach a concentration in the range between about 0.05 to about 20 mM, preferably in the range from about 0.5 to about 15 mM, such as in the range from about 1 to about 10 mM. Especially preferred is concentration of imidazole in the range from about 2 to about 9 mM, such as a concentration from about 3 to about 8 mM. most preferred is an imidazole concentration of about 4 to about 6 mM, such as a concentration about 5 mM. When using a high salt concentration buffer (often NaCl), the concentration is in the range from 100 mM up to about 1 M.

It is also preferred to add a detergent to the diafiltrated and buffer changed sample prior to the IMAC step. The detergent will normally be selected from a polyoxyethylene sorbitan fatty acid ester such as Tween 20, Tween 40, Tween 60, Tween 80, and Tween 85, an alkylaryl polyether alcohol such as Triton X100, a non-ionic detergent, and a carbohydrate based detergent such as octylglycoside. The detergent is advantageously added to reach a concentration of between about 0.05% (v/v) and 10% (v/v), such as about 0.1% (v/v).

IMAC

The IMAC step involves charging of a chromatographic medium with a divalent metal ion prior to application of the buffer exchanged sample thereto. Typically, the divalent metal ion is selected from the group consisting of $Ni^{2+}$, $Cu^{2+}$, $Zn^{2+}$, $Co^{2+}$, and $Fe^{2+}$. Preferably, the divalent metal ion is $Zn^{2+}$.

Elution of the chromatographic medium in the IMAC is performed by applying imidazole, histidine, a high salt concentration buffer, or a change of pH onto the chromatographic medium (typically in a chromatographic column). For instance, when using imidazole for elution, this is advantageously done by applying the imidazole in one single step at a concentration between about 50 mM and about 500 mM (such as between 100 and 400 mM), preferably at a concentration of about 200 mM. Alternatively, when histidine is used this is done by applying the histidine in one single step at a concentration between about 20 mM and 400 mM (such as between 50 and 200 mM), preferably about 100 mM. The high salt concentration buffer usually contains NaCl in concentrations up to about 1 or even 2 M.

SEC

The average pore size of the SEC matrix is preferably one that separates globular protein between 10 kDa and 600 kDa.

After having applied the sample to the matrix, elution is done with a phosphate or TRIS buffer or, alternatively, with a biological buffer such as HEPES. The preferred buffer is a TRIS buffer.

pH is maintained in the range of about 7 to about 8 during the SEC and preferably the pH is kept about 7.5.

If relevant and necessary (i.e. when a phosphate buffer is used in the SEC step), samples containing the EGFR family derived protein obtained from SEC, is diluted before the AIE step so as to adjust the phosphate concentration to less than 15 mM, such as to the range between 10 and 12.5 mM. However, it is surprising that the AIE can be performed at all using such a phosphate buffer concentration.

AIE

The final step in the purification procedure of the invention is at least one AIE step, whereof one is performed using a strong anion exchange matrix—in preferred embodiments, there is also a preceding step involving use of a weak anion exchange matrix. This preferably involves loading of the sample containing the EGFR family derived protein obtained after SEC on a strong or weak anion exchange matrix. Typically, the elution is performed with a buffered (phosphate, TRIS or a biological buffer such as HEPES) NaCl solution at a pH between 7 and 8, preferably about pH 7.5.

The protein obtained in the eluate after these steps has a clinical grade purity and is substantially free of contaminants derived from the insect cell culture.

It is contemplated that an AIE step utilising a weak anion exchange matrix will be applicable as a step between the IMAC and SEC steps, instead of including it as part of the concluding AIE step.

Further Optional Steps

After diafiltration it is advantageous to include a virus clearance step (e.g. with 2% Tween 20 and 0.3% TnBP) and it is further advantageous to include a virus filtration step after AIE (e.g. using a Planova 15N filter or a similar filter), where both steps are included in order to ensure that the resulting product is free of clinically unacceptable contaminants. However, in the event a virus-free system is employed, these two steps are non-essential.

HER-2 Variant of the Invention

As mentioned above, the present inventive method has been conceived when purifying a variant of the human HER-2 tumour antigen. This particular variant has proven to be especially well-suited as a vaccine agent for inducing immunological reactions against autologous HER-2 so this particular variant is also a part of the present invention.

In general, the specific use, formulation, recombinant production, suitable vectors and host cells as well as other details pertaining to this specific HER-2 variant can be found in the disclosure of WO 00/20027. Hence, in the following only a brief discussion will be provided that specifically pertains to the variant. Hence, the disclosure of WO 00/20027 is included by reference herein and provides for the necessary teachings concerning immunization with HER-2 variants and the general methods for producing these and their formulation. Also the disclosure in WO 00/20027 relating to nucleic acid vaccination against autologous HER-2 is incorporated by reference herein.

As mentioned above, another aspect of the present invention relates to an immunogenic variant of HER-2 protein that comprises the amino acid sequence set forth in SEQ ID NO: 2, residues 17-677. It is preferred that this variant is a polypeptide that consists of the amino acid sequence set forth in SEQ ID NO: 2, residues 1-677, i.e. a variant that also includes a histidinyl-rich purification tag consisting of residues 1-14 in SEQ ID NO: 2, and an aminopeptidase stop sequence consisting of residues 15 and 16 in SEQ ID NO: 2.

Also included in the present invention is a nucleic acid fragment that encodes this immunogenic variant of HER-2 protein, such as a DNA fragment. An especially preferred DNA fragment has the HER-2 variant encoding sequence set forth in SEQ ID NO: 1.

Useful tools in the recombinant production of HER-2 variants are vectors carrying the nucleic acid fragment of the invention. Especially preferred is a vector capable of autonomous replication. Typically, the vector is selected from the group consisting of a plasmid, a phage, a cosmid, a mini-chromosome, and a virus.

Expression vectors are especially preferred. A typical expression vector of the invention comprises, in the 5'→3' direction and in operable linkage, a promoter for driving expression of the nucleic acid fragment of the invention, optionally a nucleic acid sequence encoding a leader peptide enabling secretion of or integration into the membrane of the polypeptide fragment, the nucleic acid fragment of the invention, and optionally a nucleic acid sequence encoding a terminator.

For recombinant production, a host cell transformed with the vector of the invention is especially preferred. A particularly interesting host cell is an insect cell, and most preferred is a drosophila derived host cell such as an S2 cell.

Also part of the invention is a stable cell line which carries the vector of the invention and which expresses the nucleic acid fragment of the invention, and which optionally secretes or carries on its surface the immunogenic variant of HER-2 protein of the invention.

Furthermore, the invention also provides for an immunogenic composition for immunizing against HER-2 protein in a human comprising the immunogenic variant of HER-2 protein described above in admixture with a pharmaceutically acceptable carrier or vehicle and optionally an adjuvant. Details on suitable formulations can be found in WO 00/20027.

Alternatively, the vaccine may be in the form of a nucleic acid vaccine (for details concerning this technology, cf. WO 00/20027). Thus, also part of the invention is an immunogenic composition for immunizing against HER-2 protein in a human comprising the vector described above in admixture with a pharmaceutically acceptable carrier or vehicle and optionally an adjuvant Also embraced by the scope of the present invention is a method for immunizing a human against autologous HER-2, the method comprising administering, to the human being, an immunogenically effective amount of the immunogenic variant of HER-2 protein described herein or an immunogenic composition comprising the variant, or the vector described herein or an immunogenic composition comprising said vector.

It is especially preferred that this immunization method (as well as the different means for immunization described herein) is used for treating or ameliorating cancer.

PREAMBLE TO THE EXAMPLES

The following exemplification utilizes the "104.1 molecule" (cf. SEQ ID NO: 2) which is an immunogenic analogue of the cancer associated HER-2 protein. However, it will be understood by the person skilled in the art that the general teachings of the present invention are applicable for other His tagged proteins, especially those produced recombinantly in insect cell systems.

The purification process consists of the following 4 general purification steps:
1. Diafiltration with buffer change of fermentation supernatant.
2. Immobilized Metal Affinity Chromatography (IMAC)
3. Gel filtration/Size Exclusion Chromatography (SEC)
4. Anion Exchange Chromatography (AIE)

There is additionally 2 virus clearance steps included in the currently preferred process, one virus inactivation step and one virus filtration step.

Diafiltration/Buffer Exchange

The diafiltration serves three purposes 1) to concentrate the substance "104.1" 2) to remove low molecular weight substances from the fermentation medium that could interfere with the subsequent capture step, such as metal ions and 3) to change buffer into a buffer more suitable for metal chelate chromatography (IMAC). Buffer exchange takes place in one or two steps. The first step is into 50 mM phosphate buffer pH 7.0; the second step into 50 mM phosphate buffer pH 7.5 is optional. If diafiltration is performed into pH 7.5, this pH sequence seems to be critical because going directly into pH 7.5 leads to precipitation of non-identified components from the insect cell fermentation medium. Concentration is mainly performed to reduce loading time in the subsequent IMAC and to reduce consumption of buffer in the buffer exchange step and is not found essential for the process, as the subsequent IMAC by nature is a concentrating process step. The concentration scale is presently about 5 times or to a total protein concentration of the medium not exceeding 3 mg/ml (preferably not exceeding 2 mg/ml), but experiments using 10 times concentration also seem to work when protein level does not become to high and it is expected that it is possible to go higher, such as 20 or even 25 times. Further concentration than the 5 times described in the protocol may improve the process, as it would decrease the loading time on the following IMAC column.

Sample Preparation for IMAC

The diafiltrate can prior to application to the IMAC column be prepared by adding imidazole to a final concentration of 0-10 mM, when imidazole is used in eluent buffer; if no imidazole (or a similar substance) is added, we have experienced co-purification of other proteins from the insect cells with 104.1. On the other hand, when elution is made with L-Histidine, salt is added to the elution buffer instead. Furthermore, Tween 20 is added (after filtration) to a final concentration of 0.1% (v/v). Up to 5% can be applied for the IMAC step and higher concentration than 0.1% will lead to less dimer formation. Other detergents are also expected to be useful, obviously other Tween detergents (Tween 40, 60, 80 and 85).

IMAC

The substance 104.1 has a so-called His-tag in the N-terminus that has affinity for complexed divalent metal ions immobilized on the column matrix. Critical parameters are choice of divalent metal ion and choice of elution agent/method. $Ni^{2+}$, $Cu^{2+}$ and $Zn^{2+}$ can all be used as the chelating metal ion. However, $Zn^{2+}$ has provided good recovery and fewer impurities. For elution of captured 104.1 several strategies can be used. 1) Application of imidazole to the column 2) application of histidine to the column 3) application of high salt concentration buffer to the column, and 4) change of pH on the column.

The presently preferred process uses elution by application of 100 mM L-Histidine in one step. However, down to 50 mM can be used but the result is less concentrated 104.1 and lower recovery. It is also possible to use imidazole (applied as a 200 mM solution), and also this can be used at lower (down to 50 mM) concentrations with the same effect on recovery.

SEC

The example below describes that the SEC is run in TRIS buffer. However, phosphate seems to work as well, but TRIS is more suitable for the subsequent AIE than phosphate. When using phosphate or a TRIS buffer containing salt, dilution of the SEC eluate is necessary before application on the AIE column in order to reduce the phosphate concentration, and this will not be necessary with a TRIS buffer only.

If the IMAC has been run in a Tween-20 concentration higher than 0.4%, it should be adjusted to <0.4% in the SEC, as the 104.1 protein does not bind to the AIE column if the concentration of Tween-20 is higher than 0.2%. This may differ when the AIE is run in other buffer systems.

Sample Preparation for AIE Chromatography

The relevant fractions from SEC are diluted in water, 1 volume eluate+3 volumes of water, to reduce the phosphate concentration when run in phosphate as it interferes with the AIE chromatography. This issue is also discussed in the SEC paragraph.

AIE Chromatography

The critical parameters are the pH and ionic strength of the sample and buffer systems.

If the SEC has been run in TRIS, the sample preparation (dilution in water) can be avoided and the loading volume (and loading time) will be reduced. When the AIE is run in TRIS buffer including salt, the AIE is diluted in TRIS buffer until an ionic strength below 3 mS/cm is reached.

Final bulk product is analysed by SDS-PAGE, western blotting (WB), ELISA, HPLC, visual inspection, $OD_{280}$, pH, Limulus Amoebocyte Lysate (LAL) and amino acid analysis. Intermediate products are analysed by SDS-PAGE, WB, ELISA and $OD_{280}$.

As will be apparent, the AIE is preferably performed as two consecutive steps, where a first step utilises a weak anion exchange matrix and a second step utilises a strong anion exchange matrix. It is contemplated, however, that the step using a weak AIE matrix can be moved so as to be introduced between the IMAC and SEC steps.

Example 1

Culturing of HER-2 Variant 104.1

Cell Line Production

A polyclonal culture of S2 Drosophila melanogaster cells was transfected with a pMT vector (DES® system, Invitrogen) containing the gene coding for the HER2 variant 104.1; the entire nucleic acid sequence of this pMT vector is set forth in SEQ ID NO: 1. The cells were in parallel transfected with a plasmid carrying a gene conferring hygromycin resistance enabling the usage of hygromycin for selection of transfected cells.

A limited dilution technique was used for isolation of single cell clones and a Master Cell Bank (MCB) was produced from the selected cell line.

HER2 Protein AutoVac Production

One vial from the MCB is resuscitated in a T-flask and propagated in shake flasks containing ExCell420 media (JRH) at 25° C. to obtain enough biomass for the inoculation of a bioreactor. A total of $45 \times 10^9$ cells is diluted into 3000 mL with ExCell 420 supplemented with 4 mM Glutamine, 0.1% Pluronic F68, and 0.5 mL/L PD30 antifoam. The 3000 mL are used to inoculate an Applikon bioreactor (7 L working volume) where the culture grows for 3 days at 25° C., $dO_2$=500 (1000=air saturation), pH=6.5±0.1 (adjusted with 5% $H_3PO_4$ and 0.5 M NaOH), and stirred at 170 rpm.

This culture is diluted with ExCell 420 supplemented with 4 mM Glutamine, 0.1% Pluronic F68, and 0.5 mL/L PD30 antifoam to a total cell concentration of $15 \times 10^6$ cells/mL and used for inoculation of a 15 L working volume Applikon Bioreactor maintaining 25° C., $dO_2$=50% (sparging with pure oxygen), pH=6.5±0.1 (adjusted with 5% $H_3PO_4$ and 0.5 M NaOH), and stirred at 142 rpm. The culture is continuously diluted with ExCell 420 supplemented with 4 mM Glutamine and 0.1% Pluronic F68 until a total volume of 10 L is reached. The dilution rate is adjusted daily to prevent the cell number to drop below $15 \times 10^6$ cells/mL. PD30 antifoam is added manually to the culture to maintain a total concentration of 0.5 mL/L.

When filling is completed, perfusion is initiated at 1 RV/day (reactor volumes per day) using the BioSep cell (AppliSens) acoustic retention device to prevent cell loss with the removed media. At a cell concentration of $30 \times 10^6$ cells/mL, the culture is induced by addition of a total of 2 µM $CdCl_2$ (10 mM stock) to the culture and to the medium reservoir.

The fermentation medium is harvested, centrifuged to obtain a cell free supernatant, and filtrated through a PALL filter 0.8/0.22 µm. The resulting sterile supernatant is either stored at −80° C. until use (storage up to three months at −80° C. has not produced detectable stability problems) or stored at 4° C. without for up to one week (also without any detectable degradation of the protein).

The culture is terminated 10 days post induction and the residual culture media in the bioreactor is discarded.

Example 2

Diafiltration/Concentration and Buffer Change

Before use, the fermentation supernatant from Example 1 is, if kept at −80° C., thawed slowly at 4° C. over night (the last 3 to 4 hours can be performed in cold water), and thereafter stored for a maximum of 3 days at 4° C. Otherwise, the fermentation supernatant is used directly.

The fermentation supernatant is centrifuged in a Sorvall RE 5C Plus Centrifuge in SCA3000 tubes at 10,000 rpm for 15 min, at 4° C.

Diafiltration is performed in a cold room at 5±3° C. on a ProFlux M12 (Millipore) with a Pellicon 2 Cassette filter 30K 0.5 m² (Millipore, Cat# P2B030A05). The filter is before use stored in 0.1 M NaOH. Before diafiltration the filter is therefore thoroughly washed through with milli-Q water: The standard reservoir is filled with milli-Q water (3 L) and washed with water through the filter until 200 ml is left in the reservoir. This procedure is repeated 3 times until a total of 12 litres has passed through the filter. Now, diafiltration can be instigated:

A maximum of 15 L fermentation supernatant is concentrated about 5 times or to a total protein concentration of the medium not exceeding 2 mg/ml, as measured by a calorimetric method.

The recirculation pump is started. The backpressure valve should be partly locked, to give an outlet pressure that shows back pressure (e.g. 0.2 bar). The pump speed is adjusted to 30-500. The pressure difference should show 0.7-1.2 Bar, as this is when the filter's maximum capacity is used and flow over filter correspond to 3-4 L/min (e.g. Outlet P=0.2 Bar, Inlet P=1.0 bar, ΔP=0.8). Inlet pressure should show max 1.4 bar considering tubing life and performance. If a higher inlet pressure is desired, the recirculation pump pressure can be elevated (%) or the mechanical pressure on the tubing could be elevated by applying higher pressure on the tubing (scale 0-5). When the back pressure valve is closed, a higher inlet and higher outlet pressure is received. The back pressure valve should never be completely shut.

Subsequently, the concentrated fermentation supernatant is subjected to buffer exchange in one or two steps, first using 10 volumes 50 mM $Na_2HPO_4/NaH_2PO_4$, pH 7.0, and then in the optional second step by 10 volumes 50 mM $Na_2HPO_4/NaH_2PO_4$, pH 7.5: The standard reservoir on the ProFlux M12 Millipore apparatus is filled with buffer to a total volume of 3 L and also the side reservoir is filled with buffer. The setting on the apparatus is the same as when concentrating the sample.

The volume of the buffer changed sample (Vb) is measured and a sample is taken out for SDS-PAGE (Sb). The concentrated buffer changed sample is portioned into 11 ml and 50 ml lots and frozen quickly to −80° C.

Analysis of the Diafiltrate pH and ionic strength is measured to assure efficiency of the buffer exchange.

Total protein concentration is estimated spectrophotometrically at 280 nm in a 1 cm cuvette. A 10 times diluted sample (diluted in 50 mM sodium phosphate buffer pH 7.5) with 50 mM sodium phosphate buffer pH 7.5 is used as reference (using the approximation $Abs_{280}$ of 1=1 mg/ml total protein). The total protein concentration can additionally be measured by a calorimetric Bradford method (BioRad). The specific concentration of variant 104.1 is measured by ELISA and the diafiltrate is furthermore analysed by SDS-PAGE, silver stained and WB-ECL detection.

Remarks to the Diafiltration Step

It is important to start the buffer exchange at pH below 7.1 before changing to pH 7.5. Otherwise, residual components from the fermentation medium precipitate.

Diafiltered samples have been stored at −80° C. for several months without change in performance in the quantitative HER-2 ELISA. However, when thawed, even short exposure to 37° C. and 54° C. dramatically decreases the performance of the diafiltrate in the same ELISA. When kept at 0° C. (ice/water) and 4° C. after thawing from −80° C., the performance in the ELISA of the diafiltrate is stable for up to at least 4 hours.

After diafiltration, it is convenient to inactivate any virus that might be present in the diafiltrate. To do this, samples are thawed at 2-8° C. and pooled, subsequently filtered through 1.0/0.45/0.2 μm filters, whereafter 50% Tween-20, and TnBP are added to a final concentration of 2% and 0.3%, respectively. The solution is kept at 2-8° C. for 16-20 hours while gently stirring. The solution is then 0.2 μm filtered prior to the subsequent IMAC chromatography step (Example 3).

Example 3

IMAC

The general chromatographic principle for IMAC is affinity between a "tag" on the protein and a metal ion chelate complex on the column matrix. The chromatographic matrix is POROS 20MC or, preferably, 50MC (both from Applied Biosystems) and the chelating metal ion is $Zn^{2+}$. The 104.1 molecule is provided with a His-tag and the buffer system for binding of the His-tag to the column matrix is 50 mM Na $HPO_4$/NaH $PO_4$, 0.1% Tween20, pH 7.5.

2-4 mg 104.1 per ml column material is loaded and subsequently eluted using 100 mM L-Histidine, 50 mM Na $HPO_4$/NaH $PO_4$, pH 7.5, 0.1% Tween20. Alternatively, when eluting with 200 mM Imidazole, the buffer system for binding also contains 5 mM Imidazole.

Instrument: VISION Work Station (Applied Biosystems).
Software: Data analysis software for Vision, BioCAD 700E, version 3 series software, Perseptive Biosystem.
Detection: UV absorbance at λ=280 and 220 nm.
Conductivity: 0-200 mS
pH calibrated at: 7.0 and 10

Temperature: The procedure was made with buffers and column at room temperature (20-24° C.) and loading of sample on ice and fraction collection at 10° C.

Sample Preparation

To the diafiltrate containing the 104.1 molecule, 800 mM imidazole is added to a final concentration of 5 mM imidazole when an Imidazole containing buffer is used for elution in the IMAC, whereas Tween-20 is added to a final concentration of 0.1% (v/v) when L-histidine is used for elution in the IMAC. Immediately before application to the column the sample is filtrated by vacuum through a 0.22 μm filter. The sample is kept at 5±3° C. (preferably 4° C.) until application to the column where it is held on ice when applied. Handling time at room temperature should be minimized.

Column

POROS 20MC or 50 MC (preferred) in a 16×100 mm (20.1 ml) PEEK column (Applied Biosystems) packed at 2000-2500 psi—other columns depending on the scale of the purification procedure, are equally useful.

Column Charge (strip-charge) Program

Flow: 10 ml/min.
1. 5 CV of 50 mM $NaPO_4$ (abbreviation for NaH $PO_4$/Na $HPO_4$) pH 7.5, 0.1% Tween-20 (strip).
2. 5 CV $H_2O$ (Milli-Q).
3. 40 CV 100 mM $ZnCl_2$, pH 4.5.
4. 40 CV $H_2O$ (Milli-Q).
5. 20 CV 50 mM $NaPO_4$ pH 7.5, 0.1% Tween-20.

The column should be charged before each run.

Chromatography Program

Flow rate 30 ml/min, loading 5 ml/min.

Fraction collection size 9 ml, and 5 ml at the elution peak with 100 mM L-histidine (or, where applicable, at elution peak with 200 mM imidazole). Collect in a cooled (10° C.) fraction collector.

The solution containing the virus inactivated diafiltrate is loaded on to the column at 4° C. and washed with 20 CV 50 mM $NaPO_4$ pH 7.5, 0.1% Tween 20, 0.5 M NaCl followed by 5 CV of 50 mM $NaPO_4$ pH 7.5, 0.1% Tween 20 prior to elution with 50 mM $NaPO_4$ pH 7.5, 0.1% Tween 20, 100 mM Histidine.

Pool the fractions from the eluted peak from chromatogram (cf. FIG. 1). Begin pooling at peak start and collect a total of 50 ml (or 1.5 column volumes) or pool fractions based on SDS-PAGE/WB results or ELISA to a total of 50 ml. This pool can be saved over night at 5±3° C. or carried on to SEC straight away. Storage of pool up 7 days at 5±3° C., −20° C. and colder than −70° C. has shown no loss in total protein after filtration through 0.22 μm filter when analysed on SDS PAGE and WB-ECL.

Sanitization of Column

Wash the column with 5 CV 1 M NaOH, 2 M NaCl, followed by 10 CV of water. If further sanitization is needed see the RSP from the manufacturer. The column is stored in 30% EtOH at 5-30° C.

Analysis of IMAC Intermediate

Start material, flow through and eluted fractions are analysed by WB-ECL and SDS-PAGE/silver stained.

Analysis of IMAC Pool

The pool is analyzed by WB-ECL and SDS-PAGE/silver stained, HPLC and $OD_{280\ nm}$ (on 10 times diluted sample). The specific 104.1 concentration is determined by ELISA.

Example 4

SEC Gel Filtration Chromatography

The gel filtration step is run in mM Tris, 0.1% Tween-20, pH 7.5, but 50 mM Na $HPO_4$/NaH $PO_4$ can substitute the Tris as buffer system. Fifty ml from IMAC of Example 3 is loaded by Superloop (Pharmacia) on a Superdex 200 prep grade matrix.

Instrument: BioCAD 700E Work Station for Perfusion Chromatography equipped with a semi-preparative flow cell to reduce the back pressure on the column.

Software: Data analysis software for Vision, BioCAD 700E, version 3 series software, Perseptive Biosystem.

Detection: UV absorbance at λ=280 and 220 nm.
Conductivity: 0-200 mS
pH calibrated at: 7.0 and 10

Temperature: Buffers and column are room temperature (20-24° C.) and the sample is loaded directly from 4° C. Fractions containing the monomer 104.1 should be moved to 4° C. directly after collection if the collector is not cooled.

Sample Preparation

The Pool from IMAC in buffer, 50 mM Na $HPO_4$/NaH $PO_4$, 0.1% Tween20, 100 mM L-Histidine (or 200 mM Imidazole), pH 7.5, requires no special preparation. The sample should be kept cool (5±3° C.) until loading.

Column

Superdex 200 prep grade, packed in Pharmacia column XK 50×960 mm (1884 ml) at 15 ml/min as final flow rate. Load maximum 50 ml.

Chromatography Program

General flow rate 8 ml/min, load 5 ml/min.
Fraction size 9.0 ml
1. Equilibration 1.5 CV 20 mM Tris, 0.1% Tween-20, pH 7.5
2. Load: via 50 ml Super Loop, 5 ml/min
3. Elution 1.2 CV 20 mM Tris, 0.1% Tween-20, pH 7.5

The fractions from the monomer peak (cf. FIG. 2) are pooled by comparing gel and/or SE/RP-HPLC results to obtain a pure product (approximately 130 ml). This pool can be saved over night at 5±3° C. or carried on directly to the AIE chromatography of Example 5. Storage of pool up to 7 days at 5±3° C., −20° C. and colder than −70° C. has shown no loss in total protein after filtration through 0.22 μm filter when analysed by SDS PAGE and WB-ECL.

Sanitization and Cleaning of Column

The column is cleaned by running 0.5 NaOH in the reversed flow direction for 1-2 h at 6.5 ml/min (20 cm/h) followed by 3 bed volumes of buffer. For sanitization run 0.5-1.0 NaOH in reversed flow direction, 13 ml/min (40 cm/h) for 30-60 min followed by 3-5 bed volumes of sterile buffer. The column is stored in 20% ethanol at 4-8° C. For additional information confer manufactures manual.

Analysis of the SEC Intermediate

Start material and eluted fractions are analyzed by WB-ECL, SDS-PAGE/silver stained and SE/RP-HPLC.

Analysis of SEC Pool

The pool is analysed by WB-ECL and SDS-PAGE/silver stained, HPLC and $OD_{280\ nm}$. The specific 104.1 concentration is determined by ELISA.

Remarks to SEC

Make sure that the sample is kept at 5±3° C. between IMAC and loading from the Superloop.

If the fraction collector is not cooled (10° C.) make sure that fractions are moved to cold room/fridge immediately after the collection.

When the column is frequently used, a constant flow (0.2 ml/min) of 20 mM Tris, pH 7.5, 0.1% Tween 20 is applied to the column (alternatively 50 mM Na $HPO_4$/NaH $PO_4$ is used instead of 20 mM Tris and if that is the case, Tween-20 is used at 0.5%).

Example 5

AIE Chromatography

First Optional Step

Anion Exchange Chromatography is first optionally performed on a Poros 50PI matrix column. The column is equilibrated with 20 mM Tris HCl, 0.1% Tween 20 at pH 7.5. Post-equilibration, a sample is retained for bio burden testing.

The SEC eluate is loaded onto the column at 4° C. and the column washed with 20 CV 20 mM Tris HCl, 0.1% Tween 20 at pH 7.5 followed by product elution with 20 mM Tris HCl, 250 mM NaCl, 0.1% Tween 20 pH 7.5. The product pool is 0.2 μm filtered, analysed by OD280 nm, 104.1 ELISA, RP-HPLC and SE-HPLC, and stored at 2-8° C. for up to 3 days.

The Poros 50PI column is flushed with $H_2O$ (milli-Q) and cleaned with 10 CV of 2 M NaCl, 1 M NaOH before storage in 20 mM NaOH. It is sanitised with 5 CV of 0.5 M NaOH and flushed with $H_2O$ (milli-Q) before equilibration and subsequent re-use.

Mandatory Step

Anion exchange chromatography is performed at pH 7.5 (20 mM TRIS), preferably on a strong anion exchange perfusion matrix POROS 50HQ (Applied Biosystems) in a PEEK 4.6×100 mm (1.662 ml) column. 104.1 is eluted in 200 mM NaCl.

Instrument: VISION Work Station for Perfusion Chromatography.

Software: Data analysis software for Vision, BioCAD 700E, version 3 series software, Perseptive Biosystem.

Detection: UV absorbance at λ=280 and 220 nm.
Conductivity: 0-200 mS
pH calibrated at: 7.0 and 10

Temperature: The procedure was made with buffers and column at room temperature (20-24° C.) and loading of sample from ice. The fraction collector was cooled to 10° C.

Sample Preparation

If the first optional AI step is omitted, the SEC intermediate may be diluted 1+3 (to 25%) in water containing 0.1% Tween-20 under gentle magnetic stirring. Otherwise, the POROS 50PI eluate is diluted in 15 volumes 20 mM Tris HCl, 0.1% Tween-20 at pH 7.5 to reduce conductivity. The sample should be kept cool (5±3° C.) until and during loading.

Column

POROS 50HQ is packed in a 4.6×100 mm (1.662 ml) PEEK column (Applied Biosystems) at 2000-2500 psi.

Chromatography Program

General flow rate 10 ml/min, load sample 5 ml/min.
Fraction size: 9 ml during sample load, 1 ml during $1^{st}$ elution step, and 5 ml during $2^{nd}$ elution step Anion Exchange Chromatography is performed on a Poros 50HQ matrix column at 4° C. The column is equilibrated with 20 mM Tris HCl, 0.1% Tween 20 at pH 7.5. Post-equilibration a sample is retained for bio burden testing.

The sample is loaded onto the column and the column washed with 10 CV 20 mM Tris HCl, 0.1% Tween 20 at pH 7.5 and 10 CV 20 mM Tris HCl, 20 mM NaCl, 0.1% Tween 20 at pH 7.5 followed by product elution with 20 mM Tris HCl, 200 mM NaCl, 0.1% Tween 20 pH 7.5.

The fractions from the elution peak (cf. FIG. 3) are pooled by comparing gel results to obtain a concentration of more than 2.5 mg/ml or $OD_{280\ nm}$ more than 2.5. The fractions can be kept over night at 5±3° C. before pooled. Storage of pool up to 7 days at 5±3° C., −20° C. and colder than −70° C. has shown no loss in total protein after filtration through 0.22 μm filter when analysed by SDS PAGE and WB-ECL.

Sanitization of Column

Wash the column with 10 column volumes (CV) of 1 M NaOH, 2 M NaCl, followed by 20 CV of water. If further sanitization is needed confer manufacturer's manual. The column is stored in 30% ethanol at 5-30° C.

Analysis

Start material, flow through and eluted fractions are analysed by WB-ECL and SDS-PAGE/silver stained.

Analysis of AIE Pool

The pool is analysed by WB-ECL and SDS-PAGE/silver stained, Appearance and description, pH, HPLC, LAL and $OD_{280\ nm}$. (use 3 times diluted sample). The specific 104.1 concentration is determined by ELISA.

Remarks to AIE

If the SEC intermediate is diluted less than 1+3 (25%) 104.1 is detected in the run-through from the AIE due to interference from the phosphate buffer.

Up to 25 mg 104.1 has been applied to the AIE column without detectable amounts of 104.1 in the run-through.

Optional Virus Filtration

Virus filtration and the subsequent dilution and filling of drug substance take place in a Class 100 environment. Prefiltration purified bulks from one or more Poros 50HQ runs are removed from frozen storage and thawed at 2-8° C. They are then 0.1 μm filtered and passed through a Planova 20N virus filtration membrane. The filter is retained for integrity testing. The virus filtered material is adjusted to a concentration of 2.5-3.0 mg/ml by measurement of OD280 nm.

Storage of Final Bulk Product

The final bulk product is stored at temperatures colder than −70° C. in a polypropylene container or CZ vial after filtration through 0.22 μm filter.

The product thus obtained has a purity which is suitable for clinical use.

---

The invention claimed is:

1. An immunogenic HER-2 variant protein comprising residues 17-677 of the amino acid sequence set forth in SEQ ID NO: 2.

2. The immunogenic HER-2 variant protein of claim 1, consisting of residues 1-677 of the amino acid sequence set forth in SEQ ID NO: 2.

3. An immunogenic composition for generating an immune response against autologous HER-2 protein in a human comprising the immunogenic HER-2 variant protein of claim 1 in admixture with a pharmaceutically acceptable carrier or vehicle.

4. The immunogenic composition of claim 3, further comprising an adjuvant.

5. An immunogenic composition for generating an immune response against autologous HER-2 protein in a human comprising the immunogenic HER-2 variant protein of claim 2 in admixture with a pharmaceutically acceptable carrier or vehicle.

6. The immunogenic composition of claim 5, further comprising an adjuvant.

* * * * *